United States Patent
Chen et al.

[11] Patent Number: 6,165,955
[45] Date of Patent: Dec. 26, 2000

[54] MILD COLD PEARLIZING CONCENTRATES

[75] Inventors: Pu Chen; Chengshuang Zhang, both of Singapore, Singapore

[73] Assignee: Rhodia Inc., Cranbury, N.J.

[21] Appl. No.: 09/036,714

[22] Filed: Mar. 6, 1998

Related U.S. Application Data

[60] Provisional application No. 60/040,328, Mar. 6, 1997, abandoned.

[51] Int. Cl.⁷ ..................................................... A61K 7/075
[52] U.S. Cl. ......................... 510/123; 510/122; 510/125; 510/128
[58] Field of Search ..................................... 510/416, 123, 510/124, 119, 535, 479, 488, 490, 423, 424, 421, 434, 122, 128

[56] References Cited

U.S. PATENT DOCUMENTS

| | | | |
|---|---|---|---|
| 2,438,091 | 3/1948 | Lynch | 260/482 |
| 2,528,378 | 10/1950 | Mannheimer | 260/309.6 |
| 2,658,072 | 11/1953 | Kosmin | 260/513 |
| 2,826,551 | 3/1958 | Geen | 252/89 |
| 3,964,500 | 6/1976 | Drakoff | 137/7 |
| 3,976,586 | 8/1976 | Chakrabarti | 252/89 R |
| 4,152,416 | 5/1979 | Spitzer | 424/46 |
| 4,364,837 | 12/1982 | Pader | 252/173 |
| 4,902,499 | 2/1990 | Bolish, Jr. et al. | 424/70 |
| 5,403,508 | 4/1995 | Reng et al. | 510/119 |
| 5,560,873 | 10/1996 | Chen et al. | 510/123 |
| 5,573,709 | 11/1996 | Wells | 510/122 |
| 5,646,106 | 7/1997 | Chen et al. | 510/416 |

FOREIGN PATENT DOCUMENTS

| | | |
|---|---|---|
| 42 13 614 | 10/1993 | Germany . |
| 196 13 567 A1 | 9/1997 | Germany ...................... A61K 7/06 |
| 104935 | 9/1994 | Romania ...................... C07C 69/28 |
| 849 433 | 8/1958 | United Kingdom . |
| WO 96 20993 | 11/1996 | WIPO .............................. C11D 1/12 |

OTHER PUBLICATIONS

"Fatty Acids, Their Industrial Applications" E. Scott Pattison edit., Marcel Dekker Inc., Pub.; Chapter 9: J. Kalish "Fatty Acids in Cosmetics" pp. 221–232,, 1968, xp002067746 [See p. 224, Line 6–24].

*Primary Examiner*—Necholus Ogden
*Attorney, Agent, or Firm*—John Daniel Wood; Anthony P. Venturino

[57] ABSTRACT

Novel cold pearlizing concentrates provide pearlescence to personal care and beauty care products, such as shampoos and beauty soaps, providing added luster and sheen. The pearlizing agent consists essentially of a fatty acid based member selected from the group consisting of hydroxyl stearate, polyethylene glycol mono- and di-stearates, ethylene glycol mono- and distearates, stearic monoethanolamide, and mixtures thereof, wherein at least about 90% by weight of the fatty acids of said fatty acid based member consist of octadecanoic acid. The pearlizing agent has high temperature stability and is stable in shampoos which also contain a silicone emulsion, even at temperatures as high as 65° C.

43 Claims, No Drawings

MILD COLD PEARLIZING CONCENTRATES

This application claims priority under 35 USC §119 from United States Provisional Patent Application No. 60/040,328, filed Mar. 6, 1997, now abandoned.

FIELD OF THE INVENTION

The present invention relates generally to cold pearlizing concentrates used to impart pearl, iridescent sheen or glow, to beauty care and personal care products such as liquid soaps and shampoos.

BACKGROUND OF THE INVENTION

Pearlescent additives, also known as pearlizing agents, are added to beauty and personal care products such as hair and skin care products to provide a pearly appearance to the products. Chemicals which are tiny (micron size) needles or platelets often exhibit this pearly appearance. Materials which exhibit this effect are ethylene glycol mono-and di-stearate, $TiO_2$ coated mica, bismuth oxychloride, and natural mother of pearl. Many organic materials exhibit this pearlescence provided they can be produced in an appropriate needle or platelet shape. Ethylene glycol distearate (EGDS) or ethylene glycol monostearate (EGMS) are the most commonly utilized pearlizing agents.

Obtaining good pearlescence requires obtaining the appropriate crystallization. Consistency in obtaining the appropriate size and type of crystal formed is difficult especially when utilizing ethylene glycol distearate or the like. The controlled formation of EGDS crystals of the proper size to give good pearlescence depends on two major steps of the crystallization process. The first step is the solubilization by addition of EGDS to the hot (above EGDS's melting point) beauty or personal care product, for example a shampoo. Good, efficient solubilization of the EGDS depends on being above the melting point, finely emulsifying the melted EGDS, and allowing enough mixing time for the solubilization to occur. As the shampoo composition, for example, is varied, it is generally necessary to insure that it can solubilize the EGDS at a temperature greater than EGDS's melting point but then also precipitate it at a temperature less than the melting point. If a composition has too high a solubilizing capacity the EGDS may not crystallize out, may require too low of an outlet temperature (<100° F.) to crystallize or may only crystallize slowly leading to crystals that are too large. If the solubilizing capacity is too low, only part of the EGDS will be solubilized and upon cooling the unsolubilized EGDS will freeze out as large chunks.

In the second step, the precipitation or freezeout step, composition and the cooling process are important parameters. The composition should not have too high a solubilization ability as discussed. Several cooling processes are known in the art. Some methods nucleate crystals in only a portion of the composition and then mix these seed crystals back into the warmer composition. A single-pass method is better for controlling crystal size since it does not require remixing crystals into the uncooled composition. Many factors, such as flow rate, temperature and time, must be monitored and controlled to achieve appropriate crystal size. The formation of crystals depends very much on the rate of cooling. An imperfect cooling will decrease the pearlescence and the heating and cooling may have to be repeated until a satisfactory pearlescence is achieved.

Obviously, achieving consistency in the crystallization process requires constant monitoring as well as attending to adjustments. The difficulty in controlling the process translates to an inconsistency in the pearlescence of the compositions and expenditures in time and money.

A pearlizing concentrate which can be added to beauty and personal care compositions without a need for crystallization, with its requisite heating and cooling elements, can provide significant benefits. It can be added at room temperature saving energy and equipment costs and offer a more consistent pearlescence since many of the sensitive parameters of a crystallization process have been removed.

SUMMARY OF THE INVENTION

The present invention is a novel mild cold pearlizing concentrate for use in beauty and personal care compositions such as: shampoos, conditioners, lipsticks, skin creams, lotions, bubble baths, liquid dishwashing products, liquid cleaners and the like. The cold pearlizing concentrate of this invention is comprised of a pearlizing agent which consists essentially of a fatty acid based member selected from the group consisting of hydroxyl stearate, polyethylene glycol mono- and di-stearates, ethylene glycol mono- and distearates, stearic monoethanolamide, and mixtures thereof, wherein at least about 90% by weight of the fatty acids of said fatty acid based member consist of octadecanoic acid, more typically at least about 91% by weight, even more typically at least about 92% by weight, e.g. from about 93% to about 99% by weight. Typically, the fatty acid based member has a melting point above about 60° C., more typically a melting point of at least about 65° C., and even more typically from about 70° C. to about 75° C. The preferred fatty acid based member is a glycol esterified with a fatty acid composition (hereinafter "glycol ester"). As used herein, the term "melting point" is meant to include the midpoint of a melting range. The cold pearlizing concentrate can be a formulation of ingredients comprising: a pearlizing agent, a nonionic surfactant, an amphoteric surfactant, a glycol emulsifier and water. The cold pearlizing concentrate provides a brilliant sheen and pearlescence when incorporated into personal care and beauty care products.

In other words, the present invention relates to a mild, cold pearlizing concentrate comprising at most one fatty acid based pearlizing agent. The pearlizing agent contains fatty acid moieties and consists essentially of a fatty acid based member which provides the fatty acid moieties of the pearlizing agent. The fatty acid based member consisting essentially of a fatty acid based compound selected from the group consisting of hydroxyl stearate, polyethylene glycol mono- and di-stearates, ethylene glycol mono- and di-stearates, stearic monoethanolamide, and mixtures thereof At least about 90% by weight of the fatty acid moieties of the pearlizing agent consist of an octadecanoic acid moiety or, in the case of hydroxyl stearate, a hydroxyloctadecanoic acid moiety.

All percentages and ratios utilized herein are on a weight percent basis unless otherwise apparent in context.

"Comprising," as used herein, means various components can be conjointly employed. Accordingly, the terms "consisting essentially of" and "consisting of" are embodied in the term comprising.

The term "cold" as utilized herein refers to the ability of the concentrate to be added without heating to the beauty and personal care products.

DETAILED DESCRIPTION OF THE INVENTION

A stable, mild free flowing cold pearlizing concentrate of this invention is typically prepared using i) a pearlizing agent of this invention, preferably a glycol stearate; ii) a nonionic surfactant; iii) an amphoteric surfactant emulsifier and stabilizer, iv) a glycol emulsifier and v) water; to obviate the use of cocodiethanolamide and provide excellent compatibility with any ionic surfactant. The concentrate will typically be essentially free of anionic surfactants such that the concentrate is compatible with essentially any ionic surfactants that may be used in the personal care product to which this concentrate is added.

The pearlizing agent comprises from about 5% to about 40%, preferably from about 10% to about 30% and most preferably from about 15% to about 25%, by weight based on the total weight of the concentrate.

The pearlizing agent can be selected from the group consisting of hydroxyl stearate, polyethylene glycol mono- and di-stearates, ethylene glycol mono- and distearates, stearic monoethanolamide, and mixtures thereof. The preferred agents are polyethylene glycol mono- and distearates, and ethylene glycol mono- and di-stearates. The most preferred pearlizing agents for use are: ethylene glycol mono- and di-stearates.

The fatty acid based member must be derived from a fatty acid feedstock (which includes free fatty acids, carboxylate salts, fatty mono-, di- and/or tri-glycerides) which consists of at least about 90% by weight of octadecanoic acid, i.e. the saturated fatty acid having one carboxyl group (or derivative thereof) and a seventeen carbon alkyl tail covalently bonded thereto. Thus, at least about 90% by weight of the compounds of the fatty acid based member contain a fatty acid moiety containing a carboxyl group (or derivative thereof) and a seventeen carbon alkyl tail covalently bonded thereto. Stearic acid is available commercially in different grades, typically containing at least some portion of palmitic acid, i.e. the saturated fatty acid having one carboxyl group, and a fifteen carbon alkyl tail covalently bonded thereto. For example, stearic acid is available in grades of 37.5% (nominal) and 42.5% (nominal) purity. Thus, those grades of stearic acid wherein less than about 90% of the fatty acid chains are octadecanoic acid will not be useful in making the fatty acid based member used herein, unless the stearic acid is first purified to remove a sufficient number of species which are not derived from octadecanoic acid. A useful grade of stearic acid is the 95% (nominal) grade the CTFA specifications of which are 92.5% to 97.5% stearic acid and a maximum of 5% palmitic acid. A fatty acid comprised of 90% stearic acid and 10% palmitic acid should also be useful.

The pearlizing agent is most useful as a concentrate with other components, e.g. those other components as described in U.S. Ser. No. 08/542,754, filed Oct. 13, 1995, the disclosure of which is incorporated herein by reference.

A second component of the concentrate is a nonionic surfactant. This surfactant can function as an emulsifier and stabilizer in the formulation. The term "nonionic surfactant" as utilized herein encompasses mixtures of nonionic surfactants.

Examples of useful nonionic surfactants include condensates of ethylene oxide with a hydrophobic moiety which has an average hydrophilic lipophilic balance (HLB) between about 8 to about 16, and more preferably, between about 10 and about 12.5. These surfactants include the condensation products of primary or secondary aliphatic alcohols having from about 8 to about 24 carbon atoms, in either straight or branched chain configuration, with from about 2 to about 40, and preferably between about 2 and about 9 moles of ethylene oxide per mole of alcohol.

In a preferred embodiment the aliphatic alcohol comprises between about 9 and about 18 carbon atoms and is ethoxylated with between about 3 and about 12 moles of ethylene oxide per mole of aliphatic alcohol. Especially preferred are the about 12 to about 15 carbon primary alcohol ethoxylates containing about 5 to about 9 moles of ethylene oxide per mole of alcohol. One such material is commercially sold under the trade name NEODOL 25-9 by Shell Chemical Company. Other commercial nonionic surfactants include NEODOL 25-6.5 and NEODOL 25-7 sold by Shell Chemical Company.

Other suitable nonionic surfactants include the condensation products of about 6 to about 12 carbon atom alkyl phenols with about 3 to about 30, and preferably between about 5 and 14 moles of ethylene oxide. Examples of such surfactants are sold under the trade manes Igepal CO 530, Igepal CO 630, Igepal CO720 and Igepal CO 730 by Rhone-Poulenc Inc. Still other suitable nonionic surfactants are described in U.S. Pat. No. 3,976,586. To the extent necessary, this patent is expressly incorporated by reference. Most preferred for use are mixed linear alcohol ethoxylates such as Laureth-7 sold as Rhodasurf L-790 by Rhone-Poulenc Inc.

The nonionic surfactant is incorporated in the cold pearlizing concentrate in an amount of from about 3% to about 30%; preferably from about 8% to about 25% and most preferably from about 10% to 20%, based on the total weight of the concentrate.

An amphoteric surfactant comprises the third component of the present invention. The term "amphoteric surfactant" as utilized herein encompasses one or more amphoteric surfactants such as mixtures of amphoteric surfactants. Preferably, amphoteric surfactants known as the betaines, their derivatives, and mixtures thereof are incorporated to provide an enhanced pearlizing effect.

Examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates and alkyl amphopropionates wherein alkyl represents an alkyl group having 6 to 20 carbon atoms. Other suitable amphoteric surfactants include alkyl iminopropionates, alkyl iminodipropionates and alkyl amphopropylsulfonates having between 12 and 18 carbon atoms; alkyl betaines and amidopropyl betaines and alkyl sultaines and alkylamidopropylhydroxy sultaines wherein alkyl represents an alkyl group having 6 to 20 carbon atoms.

Particularly useful amphoteric surfactants include both mono and dicarboxylates such as those of the formulae:

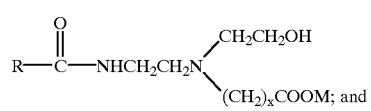

(I)

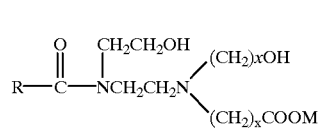

(II)

wherein R is an alkyl group of 6–20 carbon atoms, x is 1 or 2 and M is hydrogen or sodium. Mixtures of the above structures are particularly preferred.

Other formulae for the above amphoteric surfactants include the following:

Alkyl betaines

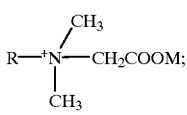  (III)

Amidopropyl betaines

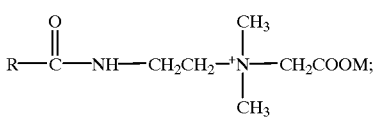  (IV)

Alkyl sultaines

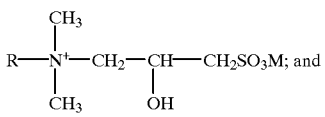  (V)

Alkyl amidopropylhydroxy sultaines

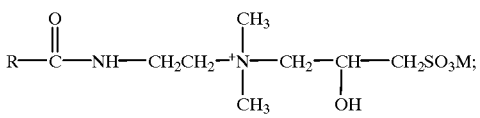  (VI)

where R is a alkyl group of 6–20 carbon atoms and M is potassium, sodium or a monovalent cation.

Of the above amphoteric surfactants, particularly preferred are the alkali salts of alkyl amphodipropionates, alkyl amphodiacetates, alkyl amphoglycinates, alkyl amphopropyl sulfonates and alkyl amphopropionates wherein alkyl represents an alkyl group having 6 to 20 carbon atoms. Even more preferred are compounds wherein the alkyl group is derived from coconut oil or is a lauryl group, for example cocoamphodipropionate. Such cocoamphodipropionate surfactants are commercially sold under the trademarks MIRANOL C2M-SF CONC. and MIRANOL FBS by Rhone-Poulenc Inc.

Other commercially useful amphoteric surfactants include:

cocoamphoacetate (sold under the trademarks MIRANOL ULTRA C-32 and MIRAPON FA), cocoamphopropionate (sold under the trademarks MIRANOL CMSF CONC. and MIRAPON FAS), cocoamphodiacetate (sold under the trademarks MIRANOL C2M CONC. and MIRAPON FB), lauroamphoacetate (sold under the trademarks MIRANOL HM CONC. and MIRAPON LA), lauroamphodiacetate (sold under the trademarks MIRANOL H2M CONC. and MIRAPON LB), lauroamphodipropionate (sold under the trademarks MIRANOL H2M-SF CONC. AND MIRAPON LBS), lauroamphodiacetate obtained from a mixture of lauric and myristic acids (sold under the trademark MIRANOL BM CONC.), and cocoamphopropyl sulfonate (sold under the trademark MIRANOL CS CONC.)

caproamphodiacetate (sold under the trademark MIRANOL S2M CONC.), caproamphoacetate (sold under the trademark MIRANOL SM CONC.), caproamphodipropionate (sold under the trademark MIRANOL S2M-SF CONC.), and stearoamphoacetate (sold under the trademark MIRANOL DM).

The most preferred amphoteric surfactant for use is cocoamphoacetate. It can be present from 0% to 10% based on the total weight of the concentrate. Preferably, cocoamphoacetate will comprise from about 1% to about 7% and most preferably from about 2% to about 4% of the concentrate.

Also useful herein are the betaines and amidobetaines which are compounds of the general structure:

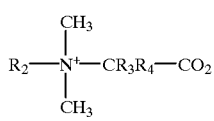

and

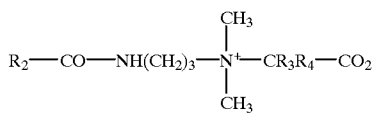

respectively wherein $R_2$ is $C_8$–$C_{22}$ alkyl or alkenyl; $R_3$ is H or $C_1$–$C_4$ alkyl; and $R_4$ is H or $C_1$–$C_4$ alkyl.

The betaines useful herein include the high alkyl betaines such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine. The sulfobetaines are also preferred and may be represented by cocodimethyl sulfopropyl betaine, stearyldimethyl sulfopropyl betaine, lauryl dimethyl sulfoethyl betaine, lauryl bis-(2-hydroxy-ethyl)sulfopropyl betaine and mixtures thereof. A particularly preferred composition utilizes cocoamidopropyl betaine.

Most preferably, the amphoteric surfactant can be cocoamphoacetate and cocoamidopropyl betaine acting as amphoteric co-emulsifiers.

The amphoteric surfactant can be present from about 2% to about 20% weight percent based on the total weight of the pearlizing concentrate. Preferably, the amphoteric will comprise from about 4% to about 16%, most preferably from about 6% to about 10%, of the pearlizing concentrate.

The fourth component consists of a glycol emulsifier. Propylene glycol (1,2, and 1,3) and other alcohols such as 1,3-butylene glycol, 2,3-butylene glycol, ethylene glycol and mixtures thereof are useful emulsifiers. The glycol emulsifier can be present from 0% to about 15%, preferably from about 1% to about 10% and most preferably from about 2% to about 5%.

For the fifth component, the remainder is water, preferably deionized. Generally, water is added in an amount of from about 20% to about 70%, preferably from about 30% to about 60%, and most preferably from about 40% to about 55% based on the total weight of the concentrate.

Non-essential optional components can be utilized in the concentrates of the present invention as a convenient means of incorporation into beauty and personal care products. Such conventional optional ingredients are well known to those skilled in the art, e.g., preservatives such as benzyl alcohol, methyl paraben, propyl paraben and imidazolidinyl urea; thickeners and viscosity modifiers such as block polymers of ethylene oxide and propylene oxide, e.g. ANTAROX F-88 (Rhone-Poulenc Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from 0% to about 2%, preferably from 0.01% to about 1.0% by weight of the concentrate.

The pH of the concentrate compositions is not critical and can be in the range of from about 2 to about 12, preferably from about 4 to about 10 and most preferably from about 6 to about 8. The pH can be adjusted using a buffer such as citric acid.

The order of addition to the mixing tank of the individual components of the concentrate is not critical nor is the reasonably elevated temperature; however, preferably the water and pearlizing agent are intimately blended at from about 50° to about 90° C., more preferably from about 70° to about 80° C. with high agitation until the pearlizing agent is emulsified. The nonionic and amphoteric surfactants are then blended into the mix until the mixture is clear. The mixture is then allowed to cool to room temperature. Generally, the concentrate can be stored at a temperature of from about 0° C. to about 45° C., preferably from about 15° C. to about 35° C. for at least one day and preferably two days in order to fully develop its pearlizing characteristics.

The cold pearlizing concentrate of the present invention can be specifically formulated into a wide variety of personal care and beauty care products. These products can be formulated by one skilled in the art utilizing conventional methods of production. The pearlizing concentrate imparts a high luster pearlescence and sheen to the products. Generally, the shampoos and soaps of the present invention can be made by merely mixing the beauty and/or personal care product together with the concentrate at room temperature.

The cold pearlizing concentrate of the present invention is particularly useful when incorporated into personal care compositions which comprise a silicone compound. As referred to herein, a silicone compound is a nonfunctionalized siloxane having a viscosity of from about 5 to about 600,000 cs (centistoke), and preferably from about 350 to about 10,000 cs, at 25° C. The so-called "rigid silicones", as described in U.S. Pat. No. 4,902,499, herein incorporated by reference, having a viscosity above 600,000 cs at 20° C., e.g., 700,000 cs plus, and a weight average molecular weight of at least about 500,000, also are useful. The silicone compound is typically a polydimethylsiloxane, typically a linear polydimethylsiloxane terminated at each end with a trimethylsilyl group. The silicone compound can be a dimethicone as specified by the CTFA, i.e. an alpha,omega-trimethylsilyl-polydimethylsiloxane having a viscosity at 25° C. of at least 25 centistokes and less than 60,000 centistokes. The silicone compound is typically used in the context of a shampoo and is added to the composition in an amount sufficient to impart improved combing and improved feel, such as softness, to the hair after shampooing.

The silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Coming Corporate Test Method CTM0004, Jul. 20, 1970.

The silicone hair conditioning agent will be used in the shampoo compositions hereof at levels of from about 0.1% to about 10% by weight of the composition, preferably from about 0.5% to about 8%, more preferably from about 1% to about 5%.

Suitable insoluble, nonvolatile silicone fluids include polyalkyl siloxanes, polyaryl siloxanes, polyalkylaryl siloxanes, polyether siloxane copolymer and mixtures thereof. However, other insoluble, nonvolatile silicone fluids having hair conditioning properties may be used. The term "nonvolatile" as used herein shall mean that the silicone material exhibits very low or no significant vapor pressure at ambient conditions, as is well understood in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. The term "silicone", as used herein, shall be synonomous with the term "polysiloxane".

The nonvolatile polyalkylsiloxane fluids that may be used include, for example, polydimethyl siloxanes. These siloxanes are available, for example, from the General Electric Company as a VISCASIL series and from Dow Coming as the Dow Coming 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Coming as 556 Cosmetic Grade Fluid.

The polyether siloxane copolymers that may be used include, for example, a polypropylene oxide modified dimethylpolysiloxane (e.g., Dow Coming DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the structure shown in U.S. Pat. No. 5,573,709, the disclosure of which is incorporated herein by reference., herein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, monophenyl-, diphenyl-, methylphenyl-, monovinyl-, and and methylvinyl-chlorosilanes, and tetra-chlorosilane, with the methyl-substituted silanes being most commonly utilized. Preferred resins are offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such unhardened form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid component to the silicone resin component is from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above.

The shampoo will contain a detersive sufactant. These include anionic, cationic, nonionic surfactants, amphoteric surfactants, zwitterionic surfactants. Examples of anionic surfactants are described in U.S. Pat. No. 5,573,709, the entire disclosure of which is incorporated by reference. Preferred anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocyl sarcosine, ammonium cocyl sulfate, ammonium lauroyl sulfate, sodium cocyl sulfate, sodium lauroyl sulfate, potassium cocyl sulfate, potassium lauryl sulfate, monoethanolamine cocyl sulfate, sodium tridecyl benzene sulfonate, or sodium dodecyl benzene sulfonate. However, the shampoo will typically be essentially free of anionc surfactants, e.g. contain less than 0.5% by weight of species that can properly be characterized as anionic surfactants. If the formulation does not include an anionic surfactant, cationic detersive surfactants can also be used.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between thehydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction havin from about 10 to about 14 carbon atoms.

4. Long chain tertiary amine oxides corresponding to the following general formula:

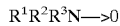

$R^1R^2R^3N\rightarrow O$ wherein R1 contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

RR'R"P$\rightarrow$O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide 3,6,9,-trioxaoctadecyldimethylphosphine oxide, cetyldimethylphosphine oxide, 3-dodecoxy-2-hydroxypropyldi (2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic detersive surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is: found in U.S. Pat. No. 5,573,709, which is incorporated herein by reference, wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxy-propane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl ) sulfopropyl betaine and the 1 like; amidobetaines and amidosulfobetaines, wherein the $RCONH(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL" ™ and described in U.S. Pat. No. 2,528,378. Another detersive surfactant optional for use in the compositions of the present invention is cocoamphocarboxy glycinate.

The most preferred shampoos of the present invention contain combinations of amphoteric surfactants, zwitterionic surfactants, and nonionic surfactants and are essentially free of anionic surfactants. The shampoos typically contain from about 0% to about 6% of amphoteric surfactants, about 0% to about 8% of zwitterionic surfactants, from 0% to about 14% of ethoxylated alkyl sulfates, and from about 0% to about 10% of an optional anionic surfactant surfactants, e.g. about 3% to about 7% alkyl sulfates, with a total surfactant level of from about 10% to about 25%.

The formulated shampoo and soap systems utilizing the cold pearlizing concentrate of the present invention can contain a variety of non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as block polymers of ethylene oxide and propylene oxide, e.g. ANTAROX F-88 (Rhone-Poulenc Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from about 0.01% to about 10%, preferably from 0.5% to about 5.0% by weight of the composition.

The following examples are provided to better describe and define the concentrate compositions of the present invention. They are for illustrative purposes only, and it is realized that changes and variations may be made with respect to these compositions that are not shown below. Such changes that do not materially alter the compositions formulation or finction are still considered to fall within the spirit and scope of the invention as recited by the claims that follow. As used in this specification and in the appended claims, all parts, percentages, ratios and the like are by weight unless otherwise apparent, in context. The terms "major" and "minor" as applied to amounts, without more, shall mean that the major amount is greater than the minor amount.

EXAMPLE I

A cold pearlizing concentrate of the present invention is prepared as follows:

| | |
|---|---|
| Ethylene Glycol Distearate | 18.0 |
| Laureth-7 | 15.0 |
| Cocoamidopropyl Betaine | 6.0 |
| Cocoamphoacetate | 2.0 |
| Propylene Glycol | 3.0 |
| Deionized Water | 56.0 |
| | 100.00 |

Ethylene glycol distearate (fatty acid distribution of $C_{18}$ at 90% minimum, acid value of 6 maximum, 1.0% free ethylene glycol, iodine value of 1.0 maximum, melting range of 68° C.–75° C., and saponification value of 188–198) is added to a mixture of water, followed by laureth-7 (RHODASURF L-790 sold by Rhône-Poulenc Inc), cocoamidopropyl betaine (MIRATAINE Bet-C-30 sold by Rhône-Poulenc Inc.), cocoamphoacetate (MIRANOL Ultra C-32 sold by Rhône-Poulenc Inc.) and propylene glycol. The mixture is then heated to 80–85° C. until the solution is clear (transparent). The solution is then allowed to cool to room temperature. The resulting concentrate has excellent pearlescence and can be utilized in a variety of personal and beauty care products.

EXAMPLE II

A cold pearlizing concentrate of the present invention is prepared as follows:

| | |
|---|---|
| Ethylene Glycol Distearate | 20.0 |
| Laureth-7 | 10.0 |
| Cocoamidopropyl Betaine | 6.0 |
| Cocoamphoacetate | 2.0 |
| Propylene Glycol | 10.0 |
| Deionized Water | 52.0 |
| | 100.00 |

Ethylene glycol distearate (fatty acid distribution of $C_{18}$ at 90% minimum, acid value of 6 maximum, 1.0% free ethylene glycol, iodine value of 1.0 maximum, melting range of 68° C.–75° C., and saponification value of 188–198) is added to a mixture of water, followed by laureth-7 (RHODASURF L-790 sold by Rhône-Poulenc Inc), cocoamidopropyl betaine (MIRATAINE Bet-C-30 sold by Rhône-Poulenc Inc.), cocoamphoacetate (MIRANOL Ultra C-32 sold by Rhône-Poulenc Poulenc Inc.) and propylene glycol. The mixture is then heated to 80–85° C. until the solution is clear (transparent). The solution is then allowed to cool to room temperature. The resulting concentrate has excellent pearlescence and can be utilized in a variety of personal and beauty care products.

EXAMPLE III

A pearlescent mild conditioning shampoo is prepared as follows:

| | |
|---|---|
| Shampoo Blend | 40.0 |
| Cocoamide DEA | 2.0 |
| Dimethiconol V 1,000,000 Emulsion | 6.0 |
| Pearlizing Concentrate of Example I | 4.0 |
| Preservative | q.s |
| Dye | q.s. |
| Fragrance | q.s. |
| Deionized Water | q.s. to 100 |

A shampoo blend of sodium methyl cocoyl taurate, cocoamidopropyl betaine, cocoamide DEA and glycerine was mixed with cocoamide DEA (ALKAMIDE DC 212/S, Rhône-Poulenc), dimethiconol emulsion (SILSOFT E 623, OSI Specialties), and the remaining conventional shampoo ingredients. The cold pearlizing concentrate of Example I is added to the premixed ingredients of the shampoo with agitation at room temperature. The resulting concentrate has excellent pearlescence and can be utilized to clean hair.

EXAMPLE IV

A pearlescent mild conditioning shampoo is prepared as follows:

| | |
|---|---|
| Shampoo Blend | 30.0 |
| Sodium Laureth Sulfate | 5.0 |
| Sodium Cocoamphoacetate (40%) | 3.0 |
| Cocoamide DEA | 2.0 |
| Dimethicone Emulsion | 6.0 |
| Pearlizing Concentrate of Example I | 4.0 |
| Preservative | q.s |
| Dye | q.s. |
| Fragrance | q.s. |
| Deionized Water | q.s. to 100 |

A shampoo blend of sodium methyl cocoyl taurate, cocoamidopropyl betaine, cocoamide DEA and glycerine was mixed with sodium laureth sulfate (RHODAPEX 3N70, Rhône-Poulenc), cocoamphoacetate (MIRANOL Ultra C-32, Rhône-Poulenc) cocoamide DEA (ALKAMIDE DC 212/S, Rhône-Poulenc), dimethicone (MIRASIL DM-E, Rhône-Poulenc), and the remaining conventional shampoo ingredients. The cold pearlizing concentrate of Example I is added to the premixed ingredients of the shampoo with agitation at room temperature. The resulting concentrate has excellent pearlescence and can be utilized to clean hair.

What is claimed is:

1. A mild, cold pearlizing concentrate comprising a mixture of:
a) at most one fatty acid based pearlizing agent, wherein said mixture comprises from about 5% to about 40% of said pearlizing agent;
b) a nonionic surfactant;
c) an amphoteric surfactant;
d) from 0% to about 15% of a glycol emulsifier; and
e) from about 20% to about 80% water;
the pearlizing agent containing fatty acid moieties,
the pearlizing agent consisting essentially of a fatty acid based member which provides the fatty acid moieties of the pearlizing agent,
the fatty acid based member consisting essentially of a fatty acid based compound selected from the group consisting of polyethylene glycol mono- and di-stearates, ethylene glycol mono- and di-stearates, stearic monoethanolamide, and mixtures thereof, wherein at least about 90% by weight of the fatty acid moieties of said fatty acid based member consist of an octadecanoic acid moiety.

2. A concentrate as claimed in claim 1 wherein at least about 91% by weight of said fatty acid moieties consist of octadecanoic acid.

3. A concentrate as claimed in claim 1 wherein at least about 92% by weight of said fatty acid moieties consist of octadecanoic acid.

4. A concentrate as claimed in claim 1 wherein from about 93% to about 99% by weight of said fatty acid moieties consist of octadecanoic acid by weight.

5. A concentrate as claimed in claim 1 wherein the fatty acid based member has a melting point above about 60° C.

6. A concentrate as claimed in claim 1 wherein the fatty acid based member has a melting point of at least about 65° C.

7. A concentrate as claimed in claim 1 wherein the fatty acid based member has a melting point from about 70° C. to about 75° C.

8. A concentrate as claimed in claim 1 wherein the fatty acid based member is a glycol esterified with a fatty acid composition.

9. A concentrate as claimed in claim 8 wherein said glycol is ethylene glycol.

10. A concentrate as claimed in claim 1 wherein the fatty acid based member is a mixture consisting essentially of mono-stearate and di-stearate esters of a glycol.

11. A concentrate as claimed in claim 1 wherein the fatty acid based member is a mixture consisting essentially of mono-stearate and di-stearate esters of ethylene glycol.

12. A concentrate as claimed in claim 1, wherein said mixture comprises:
a) from about 5% to about 40% of said pearlizing agent;
b) from about 3% to about 30% of said nonionic surfactant;
c) from about 2% to about 20% of said amphoteric surfactant;
d) from 0% to about 15% of said glycol emulsifier; and
e) the remainder water.

13. A concentrate according to claim 12 wherein said pearlizing agent is selected from the group consisting of polyethylene glycol monostearate, polyethylene glycol distearate, ethylene glycol monostearate, ethylene glycol distearate and mixtures thereof.

14. A concentrate according to claim 12 comprising from about 10% to about 30% pearlizing agent.

15. A concentrate according to claim 12 wherein said nonionic surfactant is selected from the group consisting of condensation products of primary and secondary aliphatic alcohols having from about 8 to abut 24 carbon atoms, in either straight or branched chain configuration, with from about 2 to about 40 moles of ethylene oxide per mole of alcohol; condensation products of about 6 to about 12 carbon atom alkyl phenols with about 3 to about 30 moles of ethylene oxide; and mixtures thereof.

16. A concentrate according to claim 15 wherein said nonionic surfactant comprises a condensation product of primary or secondary aliphatic alcohols having from about 9 to about 18 carbon atoms, in either straight or branched chain configuration, with from about 3 to about 12 moles of ethylene oxide per mole of alcohol.

17. A concentrate according to claim 15 wherein said nonionic surfactant comprises from about 8% to about 25% of the composition.

18. A concentrate according to claim 12 wherein said amphoteric surfactant comprises the alkali metal, alkaline earth metal, ammonium or substituted ammonium salts of alkyl amphodipropionates, alkyl amphodiacetates, alkyl amphoglycinates and alkyl amphopropionates wherein alkyl represents an alkyl group having 6 to 20 carbon atoms; alkyl iminopropionates, alkyl iminodipropionates and alkyl amphopropylsulfonates having between 12 and 18 carbon atoms; alkyl betaines and amidopropyl betaines, alkyl sultaines and alkylamidopropylhydroxy sultaines wherein alkyl represents an alkyl group having 6 to 20 carbon atoms; and mixtures thereof.

19. The concentrate according to claim 18 wherein said amphoteric surfactant is selected from the group consisting of:

a) alkali metal, alkaline earth metal, ammonium or substituted ammonium salts of alkyl amphodipropionates, alkyl amphodiacetates, alkyl amphoglycinates and alkyl amphopropionates wherein alkyl represents a lauryl or coco group;

b) alkyl betaines, amidobetaines, sulfobetaines wherein alkyl represents a lauryl or coco group; and c) mixtures thereof.

20. The concentrate of claim 19 wherein the amphoteric surfactant is selected from the group consisting of cocoamphoacetates, cocoamidopropyl betaines and mixtures thereof.

21. The concentrate of claim 19 wherein said amphoteric surfactant comprises from about 4% to about 16% of the composition.

22. A concentrate according to claim 12 wherein said concentrate comprises said glycol emulsifier and said glycol emulsifier is selected from the group consisting of: propylene glycol, butylene glycol, ethylene glycol and mixtures thereof.

23. A concentrate according to claim 12 wherein said glycol emulsifier comprises from about 1% to about 10% of the composition.

24. A concentrate according to claim 23 wherein said glycol emulsifier is propylene glycol.

25. A mild, cold pearlizing concentrate comprising at most one fatty acid based pearlizing agent, the pearlizing agent containing fatty acid moieties, the pearlizing agent consisting essentially of a fatty acid based member which provides the fatty acid moieties of the pearlizing agent, the fatty acid based member consisting essentially of a fatty acid based compound selected from the group consisting of polyethylene glycol mono- and di-stearates, ethylene glycol mono- and di-stearates, stearic monoethanolamide, and mixtures thereof, wherein at least about 90% by weight of the fatty acid moieties of said fatty acid based member consist of an octadecanoic acid moiety;

wherein said concentrate is comprised of a mixture of ingredients a) from about 5% to about 40% of said pearlizing agent;

b) from about 3% to about 30% of a nonionic surfactant;

c) from about 2% to about 20% of an amphoteric surfactant;

d) from 0% to about 15% of a glycol emulsifier; and e) the remainder water;

wherein said water comprises from about 20% to about 70% of the composition.

26. A cold pearlizing composition consisting essentially of:

a) from about 15% to about 25% of fatty acid based pearlizing agent, the pearlizing agent containing fatty acid moieties, the pearlizing agent consisting essentially of a fatty acid based member which provides the fatty acid moieties of the pearlizing agent, the fatty acid based member consisting essentially of a fatty acid based compound selected from the group consisting of ethylene glycol monostearate, ethylene glycol distearate and mixtures thereof, wherein at least about 90% by weight of the fatty acid moieties of said fatty acid based member consist of an octadecanoic acid moiety;

b) from about 10% to about 20% of a nonionic surfactant selected from the group consisting of condensation products of primary and secondary aliphatic alcohols having from about 8 to about 24 carbon atoms, in either straight or branched chain configuration, with from about 2 to about 40 moles of ethylene oxide per mole of alcohol; condensation products of about 6 to about 12 carbon atom phenols with about 3 to about 30 moles of ethylene oxide; and mixtures thereof;

c) from about 6% to about 10% of an amphoteric surfactant selected from the group consisting of cocoamphoacetates, cocoamidopropyl betaines and mixtures thereof;

d) from about 2% to about 5% of propylene glycol; and e) from about 20% to about 80% of water.

27. A method for preparing an ultra-mild pearlizing concentrate comprising intimately blending the ingredients of claim 12 at from about 60° C. to about 80° C. until the pearlizing agent is emulsified followed by cooling of the resulting blend.

28. A composition useful as a shampoo comprising a major amount by weight a detersive surfactant and a minor amount by weight of the concentrate of claim 1.

29. A composition as claimed in claim 28 wherein said shampoo is further comprised of a minor amount by weight of a silicone compound.

30. A composition as claimed in claim 29 wherein said silicone compound is an alpha,omega-trimethylsilyl-polydimethylsiloxane having a viscosity at 25° C. of at least 25 centistokes and less than 60,000 centistokes.

31. A concentrate of claim 12, wherein the concentrate is essentially free of anionic surfactant.

32. A mild, cold pearlizing concentrate comprising a mixture of:

a) at most one fatty acid based pearlizing agent which consists essentially of a fatty acid based member, wherein said mixture comprises from about 5% to about 40% of said pearlizing agent;

b) a nonionic surfactant;

c) an amphoteric surfactant;

d) from 0% to about 15% of a glycol emulsifier; and e) from about 20% to 80% water;

the fatty acid based member being derived from fatty acids, the fatty acid based member consisting essentially of a fatty acid based compound selected from the group consisting of hydroxyl stearate, polyethylene glycol mono- and di-stearates, ethylene glycol mono- and di-stearates, stearic monoethanolamide, and mixtures thereof, wherein at least about 90% by weight of the fatty acids from which said fatty acid based member is derived consist of a saturated fatty acid having 18 carbon atom.

33. A mild, cold pearlizing concentrate comprising a mixture of:
a) at most one fatty acid based pearlizing agent which consists essentially of a fatty acid based member, wherein said mixture comprises from about 5% to about 40% of said pearlizing agent;
b) a nonionic surfactant;
c) an amphoteric surfactant;
d) from 0% to about 15% of a glycol emulsifier; and
e) from about 20% to about 80% water;

the fatty acid based member being derived from fatty acids, the fatty acid based member consisting essentially of a fatty acid based compound selected from the group consisting of hydroxyl stearate, polyethylene glycol mono- and di-stearates, ethylene glycol mono- and di-stearates, stearic monoethanolamide, and mixtures thereof, wherein at least about 90% by weight of the fatty acid moieties consist of a saturated fatty acid moiety having 18 carbon atoms and only one said carbon atom is double bonded to an oxygen atom, wherein 15 of the carbon atoms are in a straight chain tail and the one carbon atom double bonded to the oxygen atom is bonded to an end of the tail.

34. A mild, cold pearlizing concentrate comprising a mixture of:
a) at most one fatty acid based pearlizing agent, the pearlizing agent containing fatty acid moieties, wherein said mixture comprises from about 5% to about 40% of said pearlizing agent;
b) a nonionic surfactant;
c) an amphoteric surfactant;
d) from 0% to about 15% of a glycol emulsifier; and
e) from about 20% to about 80% water;

the pearlizing agent consisting essentially of a fatty acid based member which provides the fatty acid moieties of the pearlizing agent, the fatty acid based member consisting essentially of a fatty acid based compound selected from the group consisting of hydroxyl stearate, wherein at least about 90% by weight of the fatty acid moieties of said fatty acid based member consist of a hydroxyloctadecanoic acid moiety.

35. A concentrate as claimed in claim 10 wherein about 93% to about 99% by weight of said fatty acid moieties consist of octadecanoic acid moieties.

36. A composition as claimed in claim 26 wherein about 93% to about 99% by weight of said fatty acid moieties consist of octadecanoic acid moieties.

37. A composition as claimed in claim 36 wherein the fatty acid based member has a melting point from about 70° C. to about 75° C.

38. A composition as claimed in claim 28 wherein about 93% to about 99% by weight of said fatty acid moieties consist of octadecanoic acid moieties.

39. A concentrate as claimed in claim 38 wherein the fatty acid based member has a melting point from about 70° C. to about 75° C.

40. A concentrate as claimed in claim 38 wherein the detersive surfactant is an anionic surfactant.

41. A concentrate as claimed in claim 38 wherein the anionic surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, and sodium dodecyl benzene sulfonate.

42. A concentrate as claimed in claim 38 wherein the anionic surfactant comprises sodium laureth sulfate.

43. A composition as claimed in claim 30 wherein about 93% to about 99% by weight of said fatty acid moieties consist of octadecanoic acid moieties.

* * * * *